(12) United States Patent
Berry et al.

(10) Patent No.: US 7,669,438 B2
(45) Date of Patent: *Mar. 2, 2010

(54) METHOD AND APPARATUS FOR ANESTHETIC GAS RECLAMATION WITH COMPRESSION STAGE

(75) Inventors: James M. Berry, Nashville, TN (US); Steve Morris, Canton, MS (US)

(73) Assignee: Anesthetic Gas Reclamation, LLC, Nashville, TN (US)

( * ) Notice: Subject to any disclaimer, the term of this patent is extended or adjusted under 35 U.S.C. 154(b) by 654 days.

This patent is subject to a terminal disclaimer.

(21) Appl. No.: 11/432,152

(22) Filed: May 11, 2006

(65) Prior Publication Data

US 2006/0254589 A1    Nov. 16, 2006

Related U.S. Application Data

(60) Provisional application No. 60/680,644, filed on May 13, 2005.

(51) Int. Cl.
| | |
|---|---|
| F25J 3/00 | (2006.01) |
| B01D 9/04 | (2006.01) |
| C02F 1/22 | (2006.01) |
| F24F 5/00 | (2006.01) |
| A62B 19/00 | (2006.01) |
| A62B 23/02 | (2006.01) |

(52) U.S. Cl. .................. 62/617; 62/532; 128/204.16; 128/205.12

(58) Field of Classification Search ............ 62/617, 62/532; 128/204.16, 205.12, 203.25, 200.24; 423/235

See application file for complete search history.

(56) References Cited

U.S. PATENT DOCUMENTS 575,714 A    1/1897    Heinzerling (Continued)

FOREIGN PATENT DOCUMENTS

| WO | WO 98/08583 | 3/1998 |
| WO | WO 01/24858 | 4/2001 |

OTHER PUBLICATIONS

U.S. Appl. No. 11/266,966, filed Nov. 4, 2005, Berry et al.

(Continued)

*Primary Examiner*—William C Doerrler
(74) *Attorney, Agent, or Firm*—Gary L. Bush; Mark D. Shelley, II; Andrews Kurth LLP

(57) ABSTRACT

A method and apparatus are disclosed for recovering and separating anesthetic gas components from waste anesthetic gases to be purged from a healthcare facility. Prior to a condensation step, a compressor is used to increase the waste anesthetic gas pressure in order to facilitate condensation of anesthetic gas components at higher temperatures and in greater amounts than through condensation at lower pressures. Condensing the anesthetic gas components from the compressed waste anesthetic gas stream is then achieved using conventional condensation systems, which remove anesthetic gases as either liquid condensates or solid frosts. A preferred embodiment of the invention may be used with existing high-flow scavenging or reclamation systems but is more preferably used with low-flow scavenging or reclamation systems, which employ intelligent waste anesthetic gas collection units to minimize the ingress of atmospheric gas when no waste anesthetic gas is to be purged from the healthcare facility.

20 Claims, 5 Drawing Sheets

U.S. PATENT DOCUMENTS

| | | | |
|---|---|---|---|
| 1,040,886 A | 10/1912 | Claude | |
| 3,348,538 A | 10/1967 | Benzel | |
| 3,517,521 A | 6/1970 | Emerson | |
| 3,592,191 A | 7/1971 | Jackson | |
| 3,714,942 A | 2/1973 | Fischel et al. | |
| 3,721,239 A | 3/1973 | Myers | |
| 3,800,793 A | 4/1974 | Marrese et al. | |
| 3,867,936 A | 2/1975 | Kelley | |
| 3,941,573 A | 3/1976 | Chapel | |
| 4,004,585 A | 1/1977 | Boehringer | |
| 4,127,163 A | 11/1978 | Reti | |
| 4,180,066 A | 12/1979 | Milliken et al. | |
| 4,181,508 A | 1/1980 | Schmid et al. | |
| 4,205,095 A | 5/1980 | Pike et al. | |
| 4,219,020 A | 8/1980 | Czajka | |
| 4,246,015 A | 1/1981 | Styring, Jr. | |
| 4,259,303 A | 3/1981 | Nakaji et al. | |
| 4,261,178 A | 4/1981 | Cain | |
| 4,265,239 A | 5/1981 | Fischer, Jr. et al. | |
| 4,281,518 A | 8/1981 | Muller et al. | |
| 4,291,689 A | 9/1981 | Hay | |
| 4,312,339 A | 1/1982 | Thompson, Sr. | |
| 4,378,984 A * | 4/1983 | Cheng et al. | 62/637 |
| 4,447,462 A | 5/1984 | Tafuri et al. | |
| 4,451,273 A | 5/1984 | Cheng et al. | |
| 4,527,558 A | 7/1985 | Hoenig | |
| 4,538,605 A | 9/1985 | Gedeon et al. | |
| 4,609,388 A | 9/1986 | Adler et al. | |
| 4,633,890 A | 1/1987 | Carden | |
| 4,653,493 A | 3/1987 | Hoppough | |
| 4,676,239 A | 6/1987 | Humphrey | |
| 4,755,201 A | 7/1988 | Eschwey et al. | |
| 4,768,347 A | 9/1988 | Manz et al. | |
| 4,832,042 A | 5/1989 | Poppendiek et al. | |
| 4,895,172 A | 1/1990 | Lindkvist | |
| 4,905,685 A | 3/1990 | Olsson et al. | |
| 4,928,685 A | 5/1990 | Gray | |
| 4,949,714 A | 8/1990 | Orr | |
| 5,033,464 A | 7/1991 | Dlcastilho | |
| 5,044,361 A | 9/1991 | Werner et al. | |
| 5,044,363 A | 9/1991 | Burkhart | |
| 5,046,491 A | 9/1991 | Derrick | |
| 5,046,492 A | 9/1991 | Stackhouse et al. | |
| 5,062,270 A | 11/1991 | Haut et al. | |
| 5,152,812 A | 10/1992 | Kovach | |
| 5,205,843 A | 4/1993 | Kaschemekat et al. | |
| 5,253,641 A | 10/1993 | Choate | |
| 5,311,862 A | 5/1994 | Blasdell et al. | |
| 5,323,623 A | 6/1994 | Carns et al. | |
| 5,339,642 A | 8/1994 | Laukhuf | |
| 5,345,928 A | 9/1994 | Lindkvist | |
| 5,370,110 A | 12/1994 | Corn | |
| 5,398,675 A | 3/1995 | Henkin et al. | |
| 5,419,317 A | 5/1995 | Blasdell et al. | |
| 5,450,728 A * | 9/1995 | Vora et al. | 62/613 |
| 5,482,033 A | 1/1996 | Engle et al. | |
| 5,507,282 A | 4/1996 | Younes | |
| 5,520,169 A * | 5/1996 | Georgieff et al. | 128/204.16 |
| 5,568,910 A | 10/1996 | Koehler et al. | |
| 5,676,133 A | 10/1997 | Hickle et al. | |
| 5,678,540 A | 10/1997 | Kock et al. | |
| 5,694,924 A | 12/1997 | Cewers | |
| 5,715,813 A | 2/1998 | Guevrekian | |
| 5,740,682 A | 4/1998 | Lavie | |
| 5,759,504 A | 6/1998 | Kanno et al. | |
| 5,769,072 A | 6/1998 | Olsson et al. | |
| 5,819,555 A * | 10/1998 | Engdahl | 62/637 |
| 5,928,411 A | 7/1999 | Falb et al. | |
| RE36,460 E | 12/1999 | Klatz et al. | |
| 6,030,591 A | 2/2000 | Tom et al. | |
| 6,076,524 A | 6/2000 | Corn | |
| 6,080,226 A | 6/2000 | Dolan et al. | |
| 6,082,133 A | 7/2000 | Barclay et al. | |
| 6,131,571 A | 10/2000 | Lampotang et al. | |
| 6,134,914 A * | 10/2000 | Eschwey et al. | 62/637 |
| 6,158,434 A | 12/2000 | Lugtigheid et al. | |
| 6,206,002 B1 | 3/2001 | Lambert | |
| 6,237,596 B1 | 5/2001 | Bohmfalk | |
| 6,328,036 B1 | 12/2001 | Emtell et al. | |
| 6,357,437 B1 | 3/2002 | Jacques | |
| 6,374,635 B1 | 4/2002 | Hayakawa et al. | |
| 6,405,539 B1 | 6/2002 | Stach et al. | |
| 6,475,266 B2 | 11/2002 | Hayashi et al. | |
| 6,488,028 B1 | 12/2002 | Lambert | |
| 6,490,883 B2 | 12/2002 | Trembley et al. | |
| 6,513,345 B1 | 2/2003 | Betting et al. | |
| 6,536,430 B1 | 3/2003 | Smith | |
| 6,729,329 B2 * | 5/2004 | Berry | 128/204.16 |
| 6,736,140 B1 | 5/2004 | Baczkowski | |
| 6,776,158 B1 | 8/2004 | Anderson et al. | |
| 6,863,067 B2 | 3/2005 | Loncar | |
| 2003/0185735 A1 * | 10/2003 | Hotta et al. | 423/239.1 |
| 2005/0155380 A1 * | 7/2005 | Rock | 62/617 |
| 2006/0254586 A1 | 11/2006 | Berry et al. | |
| 2006/0254587 A1 | 11/2006 | Berry et al. | |
| 2006/0254590 A1 | 11/2006 | Berry et al. | |

OTHER PUBLICATIONS

Brown AC, Canosa-Mas CE, Parr AD, et al.: Tropospheric lifetimes of halogenated anaesthetics. Nature 1989; 341: 635-637.

Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66-73.

McCulloch, A.: Letter to Editor regarding Langbein, et al. 1999 paper. Br J Anaesth 2000; 84 (4): 534-36.

Written Opinion of International Search Authority for PCT/US2006/18416 mailed on Sep. 24, 2007.

Examiner's First Office Action mailed Jul. 17, 2008 in connection with U.S. Appl. No. 11/266,966.

Applicant's Response to First Office Action filed Nov. 17, 2008 in connection with U.S. Appl. No. 11/266,966.

Examiner's Second Office Action mailed Dec. 30, 2008 in connection with U.S. Appl. No. 11/266,966.

Examiner's First Office Action mailed Oct. 10, 2008 in connection with U.S. Appl. 11/432,189.

Applicant's Response to First Office Action filed Apr. 9, 2009 in connection with U.S. Appl. No. 11/432,189.

Applicant's Supplemental Response to First Office Action filed Apr. 10, 2009 in connection with U.S. Appl. No. 11/432,189.

Applicant's Response to First Office Action filed Apr. 9, 2009 in connection with U.S. Appl. No. 11/432,192.

Applicant's Supplemental Response to First Office Action filed Apr. 10, 2009 in connection with U.S. Appl. No. 11/432,192.

Notice of Allowance mailed May 20, 2009 in connection with U.S. Appl. No. 11/432,189.

Notice of Allowance mailed Jul. 23, 2009 in connection with U.S. Appl. No. 11/266,966.

Notice of Allowance mailed Aug. 24, 2009 in connection with U.S. Appl. No. 11/432,192.

Examiner's Final Office Action mailed May 4, 2009 in connection with U.S. Appl. No. 11/432,192.

Applicant's Response to Final Office Action and Terminal Disclaimer Filed Aug. 4, 2009 in connection with U.S. Appl. No. 11/432,192.

Applicant's Response to Non-Final Office Action filed Jun. 1, 2009 in connection with U.S. Appl. No. 11/266,966.

R. F. Dunn, M. Zhu, B.K. Srinivas and M. M. El-Halwagi (1995), Optimal Design of Energy-Induced Separation Networks for VOC Recovery, *AIChE Symp. Ser.*, 90(303), 74-85, NY: AIChE.

* cited by examiner

METHOD AND APPARATUS FOR ANESTHETIC GAS RECLAMATION WITH COMPRESSION STAGE

CROSS REFERENCE TO RELATED APPLICATION

This application is based upon provisional application 60/680,644 filed on May 13, 2005, the priority of which is claimed. On Nov. 4, 2005, Applicants filed related non-provisional application Ser. No. 11/266,966, which claims the benefit of U.S. provisional patent application 60/680,644 filed on May 13, 2005. On May 11, 2006, Applicants filed related non-provisional application Ser. No. 11/432,192, which claims the benefit of U.S. provisional patent application 60/680,644 filed on May 13, 2005. On May 11, 2006, Applicants filed related non-provisional application Ser. No. 11/432,189, which claims the benefit of U.S. provisional patent applications 60/680,644 filed on May 13, 2005 and 60/682,249 filed on May 18, 2005.

BACKGROUND OF THE INVENTION

1. Field of the Invention

This invention concerns the treatment of waste anesthetic gases produced by one or more anesthesia delivery systems of a healthcare or other facility that use inhaled anesthetics for medical, dental, or veterinary purposes. In order to prevent atmospheric pollution, the invention pertains to the removal and reclamation of nitrous oxide, fluoro-ethers, and other halocarbons from a stream of waste anesthetic gases prior to its discharge to the atmosphere. In particular, this invention involves the removal and reclamation of anesthetic gases at elevated pressures, which allows the removal and reclamation process by condensation to be conducted at higher temperatures.

2. Backround Art

Anesthesia delivery systems in surgical facilities (medical, dental, and veterinary) produce significant quantities of waste anesthetic gases. Currently these gases are collected from the patients' exhalation by a dedicated or shared vacuum system. The healthcare facilities typically employ one or more centrally-located vacuum pumps to collect waste gases from individual anesthetizing locations. These vacuum pumps are usually oversized, because they are designed to collect exhaled anesthetics over a wide range of flow rates. Because these pumps operate continuously, the waste anesthetic gas suction system also entrains large amounts of surrounding room air from the anesthetizing locations, significantly diluting the waste anesthetic gases therein. At the central vacuum pump(s), the gas stream is often admixed with additional room air to further dilute it prior to its ejection from the facility. This dilute waste anesthetic gas/air mixture is typically pumped to a location outside of the surgical facility, where it is vented to the open atmosphere.

The waste anesthetic gases are generally collected at about 20-30° C. with a relative humidity ranging between 10 to 60 percent. The average composition of the waste gases is estimated to be (in volume percent): 25-32 percent oxygen, 60-65 percent nitrogen, 5-10 percent nitrous oxide, and 0.1-0.5 percent volatile halocarbons, including fluoro-ethers, such as isoflurane, desflurane and sevoflurane. The waste anesthetic gas may also contain trace amounts of lubricating oil vapor from the vacuum pumps.

An increasingly significant source of environmental concern, waste anesthetic gas halocarbons (similar in composition to Freon-12® and other refrigerants) have been linked to ozone depletion and to a lesser degree, global warming. The halocarbons used in anesthesia (primarily halogenated methyl ethyl ethers) now represent a significant emissions source, because other industrial and commercial halocarbon emissions have been greatly reduced by legislation and other initiatives in recent years. Although waste anesthetic gas emissions have so far escaped environmental regulation in the United States, legislative initiatives to strictly regulate waste anesthetic gas emissions will likely occur in the near future.

Several techniques have been proposed to treat waste anesthetic gases in an attempt to mitigate the growing problem of waste anesthetic gas emissions. For example, U.S. Pat. No. 4,259,303 describes the treatment of laughing gas with a catalyst, U.S. Pat. No. 5,044,363 describes the adsorption of anesthetic gases by charcoal granules, U.S. Pat. No. 5,759,504 details the destruction of anesthetic gases by heating in the presence of a catalyst, U.S. Pat. No. 5,928,411 discloses absorption of anesthetic gases by a molecular sieve, and U.S. Pat. No. 6,134,914 describes the separation of xenon from exhaled anesthetic gas. A cryogenic method for scrubbing volatile halocarbons from waste anesthetic gas is disclosed by Berry in U.S. Pat. No. 6,729,329, which is incorporated herein by reference.

Another cryogenic waste anesthetic gas condensation system has recently been disclosed by Berry, et al. in co-pending application Ser. No. 11/432,189, entitled "Anesthetic Gas Reclamation System and Method." This system uses a batch-mode frost fractionation process whereby the temperatures of the individual anesthetic gases are lowered to a point such that they condense and collect as frost on the cooling surfaces of a cold trap/fractionator. This co-pending application, filed on May 11, 2006, is incorporated herein by reference.

FIG. 1 illustrates a typical waste anesthetic gas reclamation system 10 of prior art for a healthcare facility. The system 10 includes a number of individual anesthetizing stations 15A, 15B, 15C, each having an anesthetizing machine 12A, 12B, 12C which delivers anesthesia to a patient via a mask 14A, 14B, 14C or similar device. Excess anesthetic gases, patients' exhalation, and air are collected at the masks 14A, 14B, 14C by the anesthetizing machines 12A, 12B, 12C and discharged to a common collection manifold 16. The waste anesthetic gas collection manifold 16 is typically hard plumbed into the healthcare facility, and the anesthetizing machines 12A, 12B, 12C are removably connected to the collection manifold 16 at standard waste anesthetic gas connectors 18A, 18B, 18C, e.g. 19 mm or 30 mm anesthetic connectors. The waste anesthetic gas reclamation system 10 operates at a vacuum pressure which is generated by one or more central vacuum pumps 20. The collected waste gas stream is typically passed through a check valve 35 to a condenser unit 22 consisting of one or more heat exchangers. A source of liquid oxygen, or other suitable heat sink, extracts heat from the waste anesthetic stream, condensing the anesthetic gas components. The liquid anesthetic condensate is captured in collection vessel 24, and any liquid water condensate is captured in collection vessel 23. The remaining gas stream, stripped of waste anesthetic gas components, passes through a receiver 26 and the vacuum pump(s) 20, and it is then exhausted to the atmosphere outside of the healthcare facility through vent 46.

The current methods for scavenging waste anesthetic gases from anesthetizing locations 15A, 15B, 15C in healthcare facilities generally involve drawing high flows of room air into the dedicated or shared vacuum collection manifold 16 to entrain waste anesthetic gases. The collection manifold 16 may also continuously draw in air through a number of idle anesthetizing machines 12A, 12B, 12C. On average, the collection system manifold 16 extracts between 20-30 liters of waste anesthetic gas and/or room air per minute at each anesthetizing location 15A, 15B, 15C. For a large hospital having between 20-30 operating rooms, it is estimated that waste anesthetic reclamation system 10 flow rate ranges between 500-1000 l/min. (14-35 scf/min.).

The advantages of a high-flow dilute waste gas system are that the system easily accommodates a wide range of anesthetic exhaust flows, the system is safer because little anesthetic can escape the system, and the system is more trouble-free because little maintenance is required. However, high-flow systems are energy-intensive, generally requiring large vacuum pumps 20 in order to maintain sufficient suction at a large number of anesthetizing stations 15A, 15B, 15C. For example, in order to maintain a vacuum of about 200 mm Hg at a flow rate of 1-2cubic feet per minute (cfm) at each anesthetizing station 15A, 15B, 15C, vacuum pumps of 100-200 cfm capacity are not uncommon.

Additionally, a diluted waste anesthetic gas stream is thermally inefficient. Removal of a waste gas component by condensation requires lowering the temperature of the entire flow stream to a point where the partial pressure of the gaseous waste component is equal to or greater than its saturated vapor pressure (at that temperature). Therefore, to cool the large volume of diluted waste anesthetic gas to a temperature below the saturated vapor pressure of its components, a sizeable cooling utility (i.e. a greater quantity of liquid oxygen, liquid nitrogen, etc.) is required. A method and system for increasing the efficacy and efficiency of condensation-type waste anesthetic gas scavenging and reclamation systems are thus desirable.

A low-flow scavenging system provides a more efficient means of waste anesthetic gas recovery through condensation, because a smaller volume of gas has to be cooled to the condensation temperatures of the individual gases. A low flow scavenging method, facilitated by a dynamic waste anesthetic gas collection apparatus, has recently been disclosed by Berry et al. in co-pending application Ser. No. 11/266,966, entitled "Method of Low Flow Anesthetic Gas Scavenging and Dynamic Collection Apparatus Therefor." This co-pending application, filed on Nov. 4, 2005, is incorporated herein by reference.

Typically, anesthetic gases are highly volatile substances. For a given temperature, they have a higher vapor pressure than the vapor pressure of water and other lower volatile substances. Substances with higher vapor pressures generally require greater cooling to achieve the same or similar condensate recovery as substances with lower vapor pressures. Thus, anesthetic gases need to be cooled to extremely low temperatures, i.e. cryogenic temperatures, in order to recover appreciable amounts of anesthetic as condensate. However, these extremely low temperatures approach, and in many cases, fall below the freeze point of many anesthetics. In such situations, the waste anesthetic gas stream may still contain anesthetic concentrations that could be condensed except for the undesirable freezing of the system.

Pressure, in addition to temperature, can greatly influence condensation. Elevating the pressure of the condensation system is advantageous, because it allows condensation to occur at significantly higher temperatures than would otherwise occur at lower operating pressures. This also avoids the risk and problems associated with freezing of the condensate. For these types of vapor/liquid phase equilibrium systems, the most beneficial thermodynamic characteristic is that pressure has a much larger effect on the dew point of the vapor than the freezing point of the liquid. Thus, the dew point temperature of a typical anesthetic-laden vapor stream increases with increasing pressure while its freezing point temperature stays relatively constant for varying system pressures.

The increased temperature span between the dew point of the vapor and the freeze point of the condensate, due to increases in system pressure, provides greater operational flexibilities for condensation systems. For example, less cryogenic refrigerant is needed to effect the same amount of condensation, because condensation can occur at higher temperatures. Furthermore, if a more complete separation of the anesthetic from the waste gas stream is desired, the system temperature can be lowered while maintaining an elevated pressure. This permits additional anesthetic to be condensed from the vapor phase without the associated risk of condensate freezing. Thus, a strategy may be developed to achieve the optimum separation of anesthetic by simply adjusting the condensation system pressure relative to the condensation system temperature. Of course, the relative refrigeration versus compression costs should also be considered in any cost optimization strategy.

3. Identification of Objects of the Invention

A primary object of the invention is to provide an economical system and method for removing fluoro-ethers, nitrous oxide, and other volatile halocarbons from waste anesthetic gases from a surgical or other healthcare facility before such gases are vented to the atmosphere.

Another object of the invention is to provide an economical system and method for substantially preventing atmospheric venting of fluoro-ethers and other volatile halocarbons of waste anesthetic gas while eliminating the need of prior art catalysts, charcoal granules and heating techniques.

Another object of the invention is to provide a system and method which reclaims and allows re-distillation and/or reuse of a large percentage of the nitrous oxide and/or anesthetic halocarbons used in the facility.

Another object of the invention is to provide an economical system and method which utilizes and enhances existing waste anesthetic gas reclamation systems of healthcare facilities for minimal impact and cost.

Another object of the invention is to provide an economical system and method which utilizes existing liquid oxygen and/or liquid nitrogen storage and delivery systems of healthcare facilities for energy efficiency and minimal impact during the reclamation system installation.

Another object of the invention is to provide an economical system and method for separating various removed nitrous oxide, fluoro-ethers, and other volatile halocarbon components based on their characteristic bubble and dew points.

Another object of the invention is to provide an economical system and method for increasing the efficacy and efficiency of condensation-type waste anesthetic scavenging systems.

Another object of the invention is to provide a flexible system and method for increasing the efficacy and efficiency of condensation-type waste anesthetic scavenging system by operating the system under varying pressures and temperatures.

Other objects, features, and advantages of the invention will be apparent to one skilled in the art from the following specification and drawings.

SUMMARY OF THE INVENTION

The objects identified above, as well as other advantages and features, are preferably embodied in a system and method for the removal of nitrous oxide and volatile halocarbon gas components from waste anesthetic gases using one or more compression stages to elevate the pressure of the waste anesthetic gas stream prior to anesthetic reclamation by condensation. The waste anesthetic gas stream at elevated pressure is cooled in a condenser such that the temperature of the nitrous oxide and other anesthetic halocarbons are lowered to a point where the vapors condense as a removal liquid or collect as frost on the cooling surfaces of the condenser. In other words, to recover the anesthetic components from the effluent gas, the nitrous oxide and halocarbon components in the waste anesthetic gas are compressed and cooled to either condense them into a removable liquid condensate or solidify them onto the cooling coil surfaces of a heat exchanger/condenser. Whether the anesthetic gas components condense as a liquid or deposit as a solid depends on the operational temperature and pressure of the condenser/heat exchanger.

Compression of the waste anesthetic gas to a level above atmospheric pressure is advantageous, because the higher pressure essentially elevates the temperature at which saturation and condensation of the anesthetic gas can occur. Thus, compression of the gas above atmospheric pressure allows the same fraction of anesthetic to be removed by condensation at a higher temperature as would otherwise have occurred by condensation at atmospheric pressure and at a lower temperature. Moreover, a greater fraction of anesthetic may be condensed from the vapor phase as the temperature of the compressed waste anesthetic gas is lowered from this higher temperature. A strategy may be developed to achieve the optimum separation of anesthetic by simply manipulating the condensation system pressure relative to the condensation system temperature. Furthermore, energy and cost saving may be possible when the relative refrigeration versus compression costs are factored into the strategy.

In a preferred embodiment of the invention, a compressor unit consisting of one or more compression stages is located within the waste anesthetic gas scavenger system between the waste anesthetic gas collection unit and the condensation unit. The compressor unit is sized to compress the anesthetic waste gas from the collection unit to a pressure up to 50 psig for subsequent treatment in a condensation system using a refrigerant, i.e. liquid oxygen, liquid nitrogen, etc., supplied by a hospital or other medical, dental, or veterinary facility. In an alternative embodiment, the waste anesthetic gas stream is compressed to pressures well above 50 psig to take advantage of attendant increases in separation efficiency and fractional extraction. However, in this alternative embodiment, a separate refrigerant supply for the condenser is desirable in order to avoid the risk of contaminating the healthcare facility's gas supplies should an internal leak within the condenser occur.

In a preferred embodiment, the compressed waste anesthetic gas is passed through a multi-stage condenser/heat exchanger wherein heat from the waste anesthetic gas stream is exchanged with the liquid refrigerant. In the first condenser stage, any water vapor in the waste anesthetic gas stream is condensed and extracted. In subsequent condenser stages, the temperature of the compressed gas stream is reduced to a point where the partial pressure of each gaseous waste component is equal to or greater than its saturated vapor pressure (at that temperature and elevated pressure). At atmospheric pressure, the anesthetics are extracted from the waste gas into their purified components most efficiently at temperatures near their individual freezing points. However, separation of the anesthetic vapor mixture is achieved at temperatures higher than their individual freezing points when the waste anesthetic gas stream is condensed at elevated pressure. After condensation and extraction of the anesthetic gases into their purified components, the remainder of the anesthetic gas is vented to atmosphere. However, in a preferred embodiment, the waste gas stream is passed through an expansion valve to further cool the gas via the Joule-Thompson effect. This may also induce additional condensation of anesthetic components from the waste gas. More preferably, the waste gas stream is passed through a small turbine, which recovers the potential energy of compression and may induce additional condensation.

BRIEF DESCRIPTION OF THE DRAWINGS

The invention is described in detail hereinafter on the basis of the embodiments represented in the accompanying figures, in which.

DESCRIPTION OF THE PREFERRED
EMBODIMENT OF THE INVENTION

Figure 1:
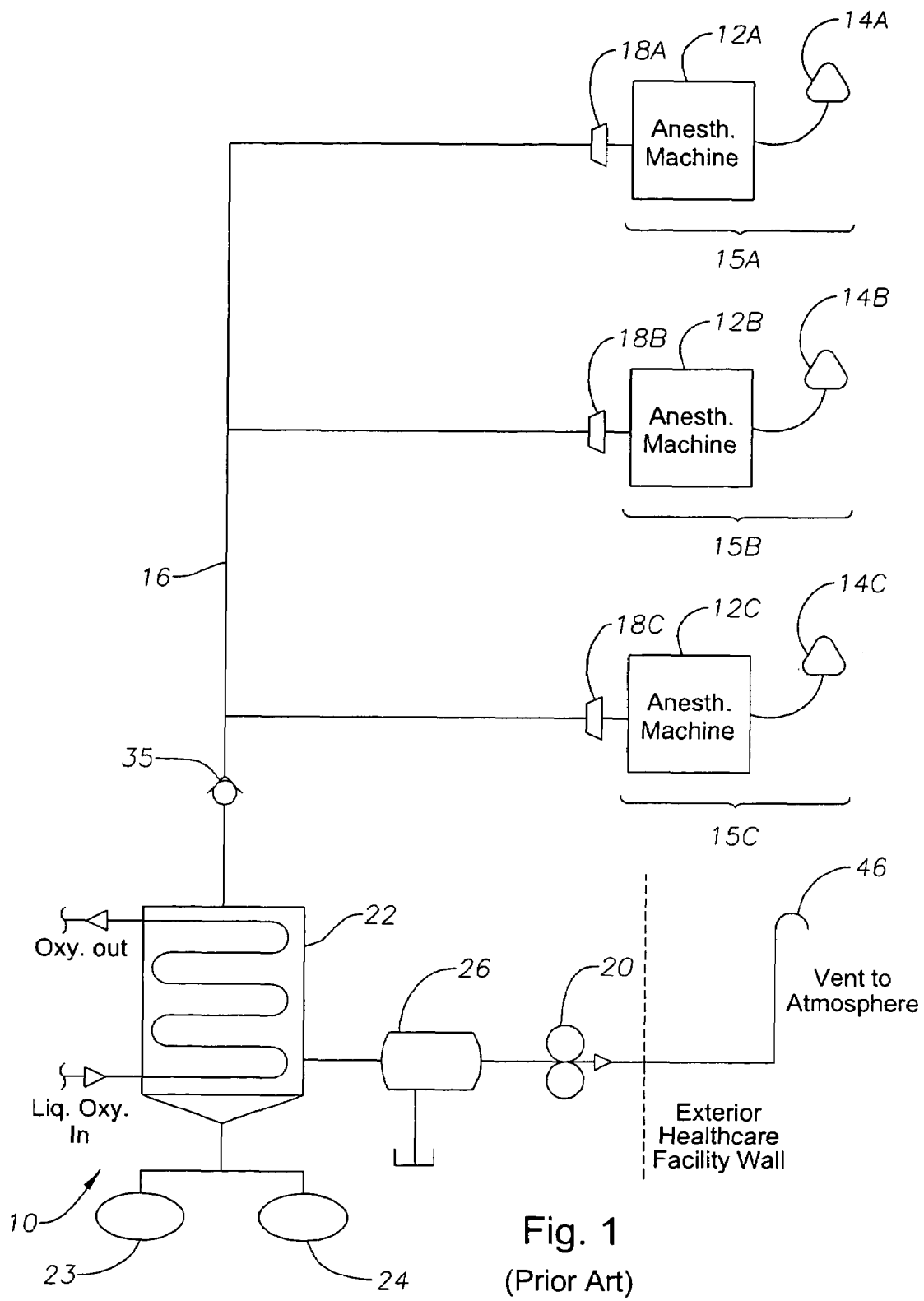
FIG. 1 illustrates in schematic form a high-flow waste anesthetic gas reclamation system of prior art by which fluoro-ethers and other volatile halocarbon gas components of waste anesthetic gases are separated from the collected gas stream by condensation before the waste gas stream is vented to the atmosphere.
Figure 2:
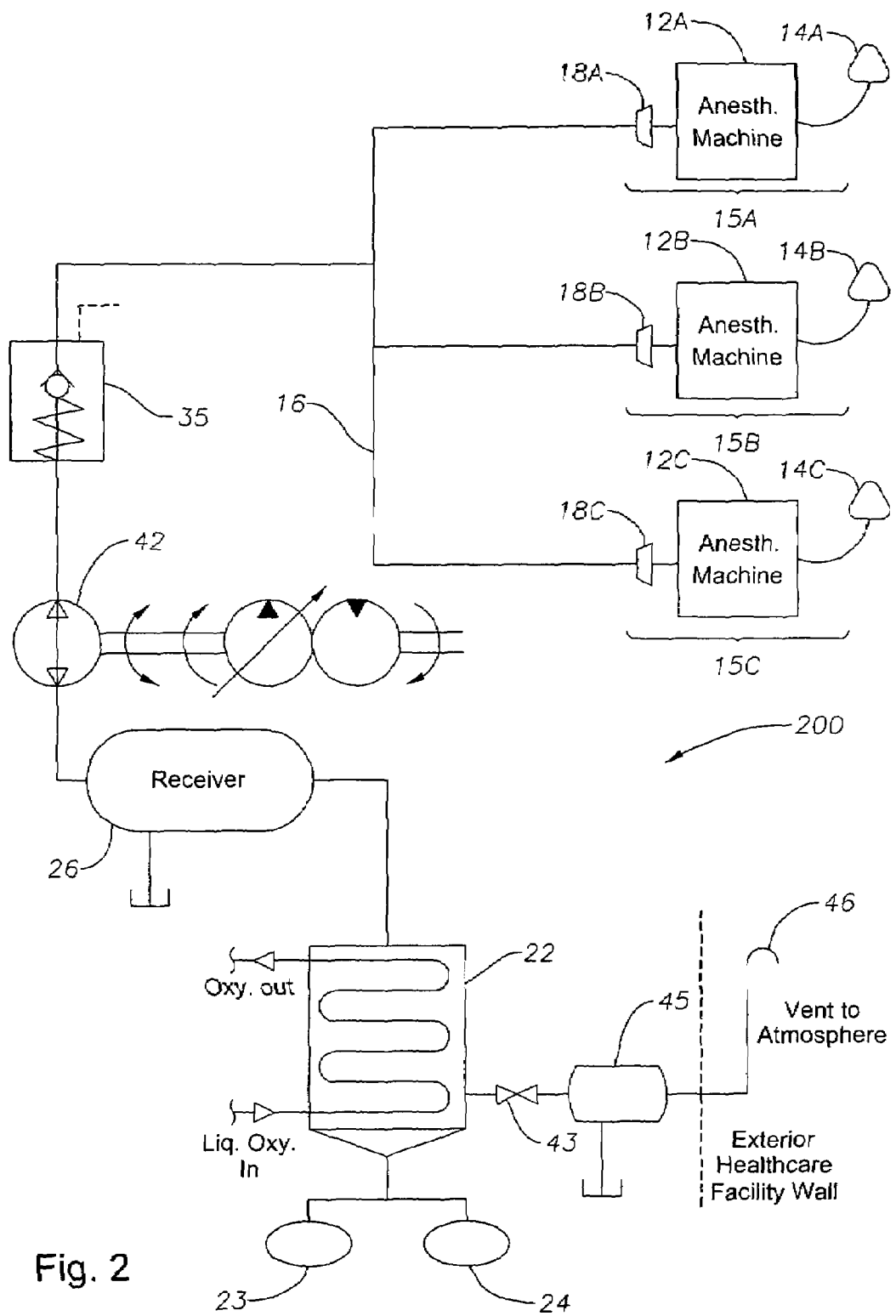
FIG. 2 illustrates in schematic form a preferred embodiment according to the invention of a high-flow waste anesthetic gas reclamation system which includes one or more high-flow waste anesthetic gas collection units, a compressor consisting of one or more compression stages, a single or multiple stage condenser/heat exchanger unit, and an expansion valve to induce additional anesthetic gas condensation.

FIG. 2 illustrates a high-flow waste anesthetic gas collection and reclamation system 200 according to a preferred embodiment of the invention for use in a hospital, surgical, dental, veterinary, or other healthcare facility. The reclamation system 200 is similar to the previously described prior art waste anesthetic gas reclamation system 10 of FIG. 1 except for the inclusion of an expansion valve 43 and one or more compression stages provided by a compressor 42. Compressor 42 is preferably disposed between the waste anesthetic gas collection units 15A, 15B, 15C and the condenser 22. Expansion valve 43 is preferably disposed between the condenser 22 and the receiver 45.

As shown in FIG. 2, excess anesthetic gases, patients' exhalation, and air are collected at masks 14A, 14B, 14C by the anesthetizing machines 12A, 12B, 12C and discharged to a common collection manifold 16. The waste anesthetic gas collection manifold 16 is typically hard plumbed into the healthcare facility, and the anesthetizing machines 12A, 12B, 12C are removably connected to the collection manifold 16 at standard waste anesthetic gas connectors 18A, 18B, 18C, e.g. 19 mm or 30 mm anesthetic connectors. The waste anesthetic gas collection manifold 16 operates at a slight vacuum pressure, e.g. 5 cm, which is generated by compressor 42. From the collection manifold 16, the collected waste anesthetic gases are passed through a check valve 35 into the first stage of a single stage or multiple stage compressor 42.

In a preferred embodiment, the compressor 42 is sized to compress the anesthetic waste gas from the collection units 15A, 15B, 15C to a pressure up to 50 psig for subsequent treatment in a condensation unit 22. Pressures above 50 psig are preferable in order to take advantage of attendant increases in separation efficiency and fractional extraction. Multistage compressors are used to avoid the problems associated with high compression ratios, such as high discharge temperatures and increased mechanical breakdowns. As a result, compressor manufacturers recommend a compression ratio of no more than 10:1, especially for low-temperature applications. Multistage compressors can also be more economical than single stage compressors because of the attendant power cost savings attributable to compression stages having smaller compression ratios. However, the compressor 42 of system 200 needs only a single compression stage, because a compression ratio of no more than 10:1 is anticipated.

The condenser 22 preferably uses a liquid oxygen, liquid nitrogen, or similar refrigerant obtained from the common supply of these liquefied gases normally available at a hospital or other medical, dental, or veterinary facility. If the waste anesthetic gas is compressed above the facility's gas supply pressure (e.g. 50 psig), then contamination of the common refrigerant supply with waste anesthetic is possible should an internal leak occur within the condenser unit 22. In an alternative preferred embodiment, the waste anesthetic gas stream is compressed to pressures well above 50 psig to take advantage of the attendant increases in separation efficiency and fractional extraction. For compression above 50 psig, however, a separate supply of liquid oxygen, liquid nitrogen, or similar refrigerant, is recommended in order to avoid the risk of contaminating the common gas supplies of the healthcare facility with waste anesthetic should an internal leak occur within the condenser unit 22.

After compression, the waste anesthetic gas flows through a collection vessel or receiver 26 which allows any liquid condensed due to compression to be removed and separated from the compressed waste anesthetic gas stream. Prior to condensation recovery of the anesthetic components, any water vapor in the gas stream should be removed to prevent freezing of the liquid water condensate in the condenser 22. A preferred method to remove water vapor from the waste anesthetic gas stream is to use a first condenser stage 222A (FIG. 3), however, alternative water removal processes (not shown) may be employed, such as desiccation, adsorption, filtration, semi-permeable or hydrophobic membranes, etc. These various gas drying methods may be used at any point prior to the condensation of the anesthetic gases, including before the compression stage.

Figure 3:
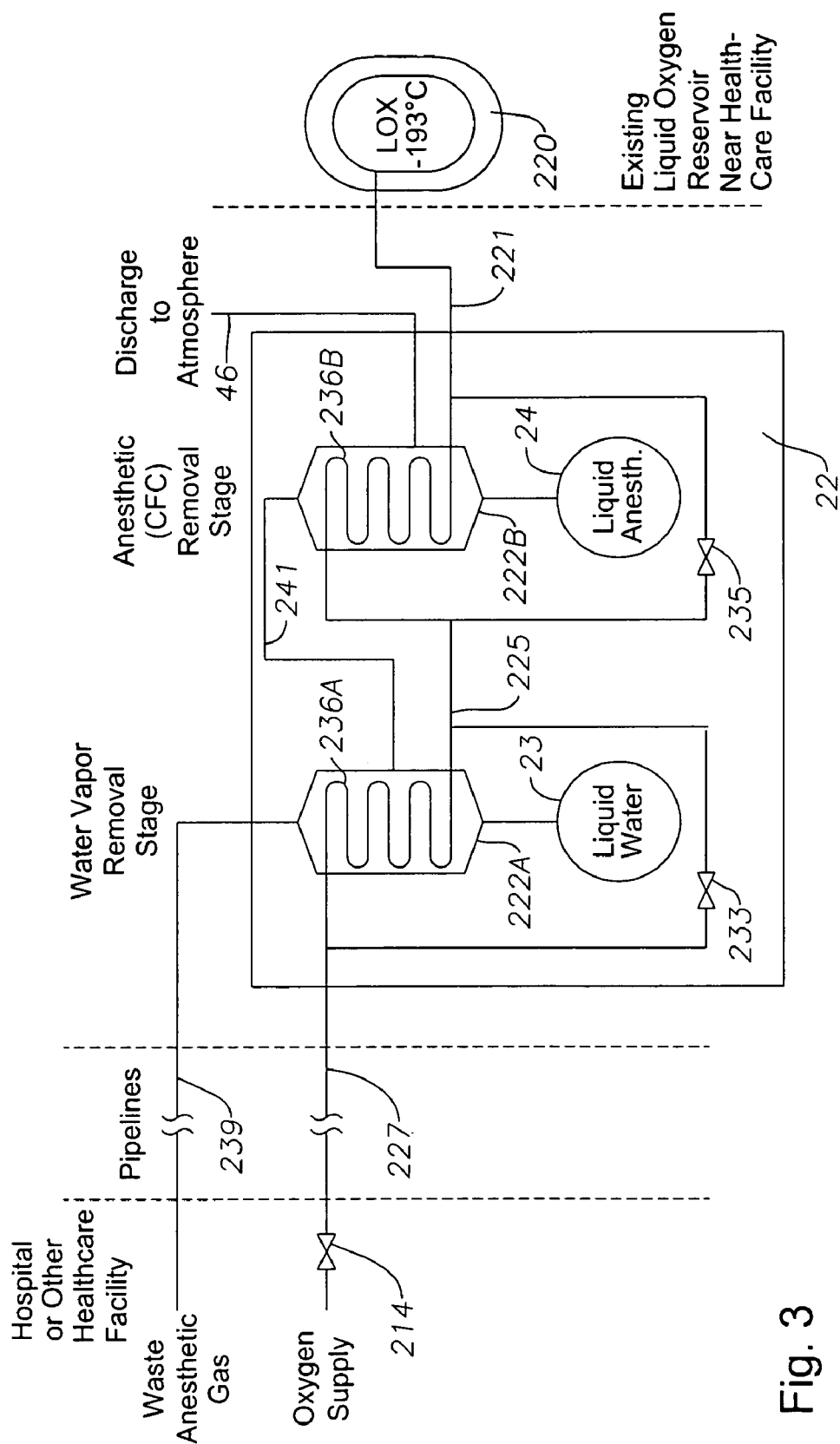
FIG. 3 illustrates in schematic form the process and system by which halocarbon gas components of waste anesthetic gases are liquefied using a source of liquefied oxygen at a healthcare facility for removal of such gas components prior to venting of the waste anesthetic gases to the atmosphere.
Figure 4:
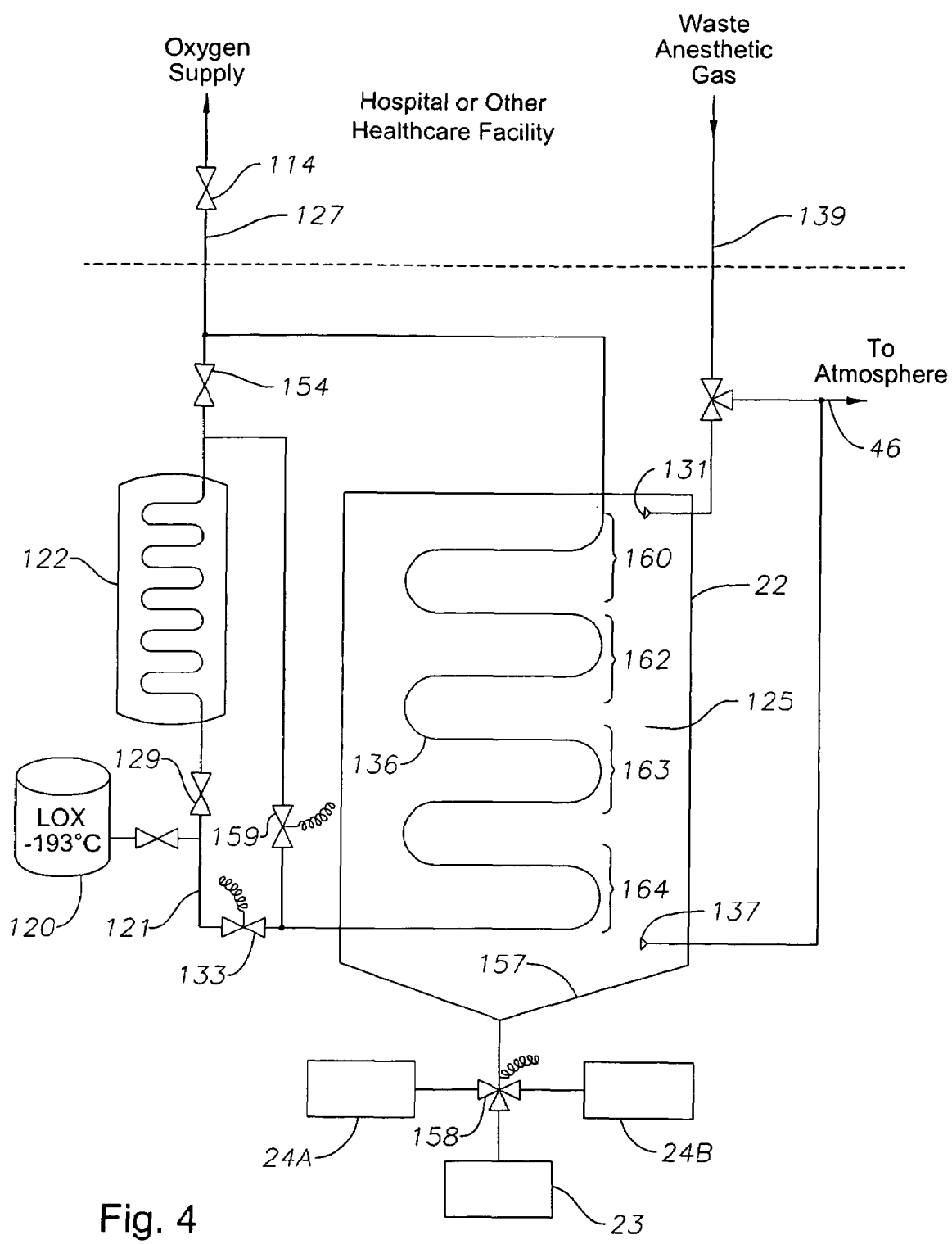
FIG. 4 illustrates in schematic form the process and system by which fluoro-ethers and other volatile halocarbon gas components of waste anesthetic gases are separated therefrom and subsequently fractionated by sequential thawing and collection of the resultant liquid halocarbon prior to venting of the waste anesthetic gases to atmosphere, using as a heat sink for the process a source of liquefied oxygen.

The compressed waste anesthetic gas stream is then cooled in a single or multiple stage condenser 22 such that the temperature of the nitrous oxide and other anesthetic halocarbons are lowered to a point where the vapors either condense as a removal liquid on the condenser coils 236B (FIG. 3) or collect as frost on the condenser coils 136 (FIG. 4). The temperature and pressure at which the condensation process is conducted controls whether the anesthetic gas components are condensed as a removable liquid or deposited as a frost.

After the anesthetic components are removed through condensation, the remaining waste gas (mainly composed of entrained air) may be vented to the atmosphere 46. Preferably, the compressed waste gas is first passed through an expansion valve 43 and a receiver 45 prior to atmospheric venting 46. The expansion valve 43 reduces the compressed waste gas to atmospheric pressure and further cools the compressed waste gas via the Joule-Thompson effect. Any additional anesthetic components in the waste gas may be condensed through Joule-Thompson adiabatic expansion. These anesthetic condensates are collected in the receiver 45 prior to the atmospheric discharge 46 of the waste gas. More preferably, however, the compressed waste gas is first throttled through a small turbine 44 (FIG. 5) or similar device and a receiver 45 prior to atmospheric release 46 (FIG. 5) in order to capture the potential energy of the compressed waste gas. The captured energy may then be used to power the compressor 42 or supply other energy requirements of the method and system. Any anesthetic components condensed by expansion of the waste gas in turbine 44 are likewise collected in the receiver 45 prior to the atmospheric discharge 46 of the waste gas.

Moreover, prior to atmospheric discharge, heat integration of the cooled waste gas with streams to be cooled may reduce the overall cooling utility of the method and system. For example, compression of the waste anesthetic gas stream causes the temperature of the gas stream to increase. The cooled waste gas stream to be vented 46 could be used to cool this compressed waste anesthetic gas stream prior to condensation in order to reduce the overall refrigerant requirement of the heat exchanger/condenser 22.

Berry discloses two cryogenic methods for recovering volatile halocarbons from waste anesthetic gas. First, U.S. Pat. No. 6,729,329 discloses the use of liquid oxygen to condense anesthetic gas components into recoverable liquid condensates. FIG. 3 generally illustrates the system and method of the '329 patent, which has been modified for an entering compressed waste anesthetic gas stream. Because the dew point temperature of a typical anesthetic-laden vapor stream increases with increasing pressure, this first recovery method is significantly and advantageously affected by the increased pressure of the waste anesthetic gas stream.

A condenser unit 22 is provided which includes first and second condensers 222A and 222B. The outlet line 221 for liquid oxygen from supply tank 220 is fluidly connected to the condensing coils 236B of the second vessel 222B. The outlet of condensing coils 236B is fluidly connected via flow line 225 to the inlet of coils 236A of first vessel 222A. The outlet of coils 236A is fluidly connected via flow line 227 to valve 214 and flow lines connected thereto (not shown) of the healthcare facility.

A flow line 239 connects the waste anesthetic gas flow lines from receiver 26 (FIGS. 2 and 5) of the healthcare facility to an inlet of heat exchanger/condenser 222A. The temperature of oxygen flowing at the inlet of the coils 236A is controlled thermostatically by valve 233 such that the temperature of the oxygen supply at valve 214 is approximately room temperature, i.e. about 25° C. The waste anesthetic gas enters heat exchanger/condenser 222A via flow line 239 at an elevated temperature due to compression. The compressed waste anesthetic gas enters at the top or entrance of heat exchanger/condenser 222A and passes downward over coils 236A wherein it exchanges heat with the liquid oxygen flowing countercurrently through the coils 236A. Water vapor in the compressed waste anesthetic gas condenses to liquid water at a specific temperature (above 0° C.), which is dependent upon the pressure of the compressed waste anesthetic gas stream. The liquid water then falls by gravity to tank 23 for storage and removal.

The cooled compressed gas near the bottom of vessel 222A is conducted via flow line 241 to the top or entrance of heat exchanger/condenser 222B where it is applied at a temperature greater than 0° C. The cooled compressed gas applied to the top of heat exchanger/condenser 222B passes over coils 236B wherein it exchanges heat with the liquid oxygen flowing countercurrently through the coils 236B. The oxygen from flow line 221 enters the coils 236B at a temperature of approximately −150° C. and leaves the coils 236B via flow line 225 at an increased temperature. If necessary, an intermediate bypass valve 235 may be provided in line 221 to bring the temperature in line 225 at the inlet of coils 236A to approximately 0° C. The temperature of the compressed waste anesthetic gas from flow line 241 is lowered while passing over the coils 236B such that the halocarbons of the waste gas are liquefied and discharged into a collection tank 24. The remainder of the compressed waste gas, i.e., those components which are not harmful to the atmosphere, are vented to the atmosphere via flow line 46, throttled through an expansion valve 43 (FIG. 2) to induce additional anesthetic condensation, throttled through a small turbine 44 (FIG. 5) to capture the potential energy of the compressed gas, or subjected to further processing by existing catalytic techniques (not shown).

Second, co-pending application Ser. No. 11/432,189, entitled "Anesthetic Gas Reclamation System and Method," discloses the use of a batch-mode frost fractionation process whereby the temperatures of the individual anesthetic gases are lowered to a point such that they collect as frost on the cooling surfaces of a cold trap/fractionator. The cold trap/fractionator is periodically cycled through a thawing stage, during which the cooling surfaces, caked with frost gas components deposited from the waste anesthetic gas passing thereby, are gently warmed to sequentially separate and collect the trapped components. FIG. 4 generally illustrates the system and method of the this co-pending patent application, which has been modified for an entering compressed waste anesthetic gas stream. However, because the freezing point temperature of a typical anesthetic-laden vapor stream remains relatively constant for varying system pressures, this second system and method of waste anesthetic reclamation is not as significantly affected by increases in the pressure of the waste anesthetic gas stream.

As shown in FIG. 4, a condenser unit 22 consisting of a cold trap/fractionator 125 is provided with cooling coils 136 therein. The outlet line 121 for liquid oxygen from supply tank 120 is fluidly connected to the condensing coils 136 of cold trap/fractionator 125. The flow of oxygen at the inlet of the coils 136 is controlled thermostatically by valve 133. The existing heat exchanger 122, used to warm the liquid oxygen, preferably remains in place fluidly connected in parallel with cold trap/fractionator 125 between liquid oxygen tank 120 and oxygen flow line 127 to warm the oxygen when the cold trap/fractionator 125 does not keep pace with facility oxygen demand, is operating in its thaw cycle as described below, or is out of service, for maintenance or repair, for example. Valve 129 normally remains closed when heat exchanger 122 is not in use. The oxygen from flow line 121 enters the coils 136 at a temperature of approximately −150° C. and leaves the coils 136 at approximately 0° C. Oxygen intended for use by the healthcare facility may be further warmed by a subsequent process or mixed with warmer oxygen effluent from heat exchanger 122 to reach room temperature or an appropriate temperature. The outlet of coils 136 is fluidly connected via flow line 127 to valve 114 and flow lines connected thereto (not shown) of the healthcare facility.

A flow line 139 connects the waste anesthetic gas flow lines from receiver 26 (FIGS. 2 and 5) of the healthcare facility to an inlet 131 of heat exchanger/condenser 125. The temperature of the waste anesthetic gas enters heat exchanger/condenser 125 via flow line 139 at an elevated temperature due to compression. The compressed waste anesthetic gas enters at the top or entrance 131 of heat exchanger/condenser 125 and passes downward over coils 136 wherein it exchanges heat with the liquid oxygen flowing countercurrently through the coils 136. The waste anesthetic gas leaves the heat exchanger/condenser 125 through fitting 137 and is purged to the atmosphere via flow line 46.

This countercurrent heat exchanger arrangement results in a temperature gradient where the top of the cold trap/fractionator 125 is the warmest and where the bottom of the cold trap/fractionator 125 is the coldest. The upper region 160 of the cooling coils 136 of the cold trap/fractionator 125 cools the compressed waste anesthetic gas to a temperature of approximately −5° C. to extract water vapor as frost on the coils 136. The upper middle region 162 of the cooling coils 136 next cools the compressed waste anesthetic gas to a temperature of approximately −60° C. which allows sevoflurane to condense and solidify onto the coils 136. Next, the lower middle region 163 extracts nitrous oxide by condensation and solidification at a temperature of approximately −90° C., and finally the lower region 164 of the cooling coils 136 extracts isoflurane and desflurane by condensation and solidification onto the coils 136 at the lowest temperature (between approximately −100° C. and −110° C.). Alternatively, if heat exchanger/condenser 125 is operated under low pressure (i.e. vacuum pressure), then the anesthetic components may be desublimated/deposited directly onto coils 136 without first entering a liquid phase. The remainder of the compressed waste anesthetic gas, i.e., those components which are not harmful to the atmosphere, are vented to the atmosphere via flow line 46, throttled through an expansion valve 43 (FIG. 2) to induce additional anesthetic condensation, throttled through a small turbine 44 (FIG. 5) to capture the potential energy of the compressed gas, or subjected to further processing by existing catalytic techniques.

The cold trap/fractionator 125 is periodically cycled through a thaw process in order to defrost the cooling coils 136. Thawing of coils 136 is effectuated by reducing or prohibiting the flow of liquid oxygen therethrough by thermostatic control valve 133. This allows the cold trap/fractionator 125 to warm to room temperature through heat transfer with its ambient surroundings. In an alternate embodiment, warmed oxygen from heat exchanger 122 may be partially or completely directed through the cooling coils 136 by simultaneously opening valve 159 and closing valves 133, 154. In yet a third embodiment, another fluid (not shown) may be directed through cooling coils 136 to achieve a controlled thaw.

A funnel-shaped hopper 157 forms the lowest point of heat exchanger/condenser 125 and preferably drains into a 4-way selector valve 158, which in turn is fluidly coupled to anesthetic collection tanks 24A, 24B and a water collection tank 23. As the temperature of the coils 136 increases above approximately −100° C. during the thawing stage, desflurane (melting point of approximately −108° C. at atmospheric pressure) and isoflurane (melting point of approximately −103° C. at atmospheric pressure) melt from the lower region 164 of cold trap/fractionator 125 and collect in the hopper 157. Selector valve 158 is concurrently aligned to allow the liquid desflurane and isoflurane to gravity feed into one of the collection tanks 24A, 24B. As the cold trap/fractionator continues to warm above −90° C., the trapped nitrous oxide melts from the lower middle region 163 of cold trap/fractionator 125 and collects in the hopper 157. Selector valve 158 is concurrently aligned to allow the liquid nitrous oxide to gravity feed into one of the collection tanks 24A, 24B. As the temperature warms further still above −65° C., sevoflurane (melting point of approximately −67° C. at atmospheric pressure) melts from the upper middle region 162 of the cooling coils 136 and collects in the hopper 157. Selector valve 158 is concurrently aligned to allow the liquid sevoflurane to gravity feed into one of the collection tanks 24A, 24B. Likewise, as the cold trap/fractionator 125 continues to warm, the water vapor frost will melt above 0° C. from the upper region 160 and be channeled by selector valve 158 into the water collection tank 23. By this method, the fluoro-ethers are fractionated as they are removed from the waste anesthetic gas.

Figure 5:
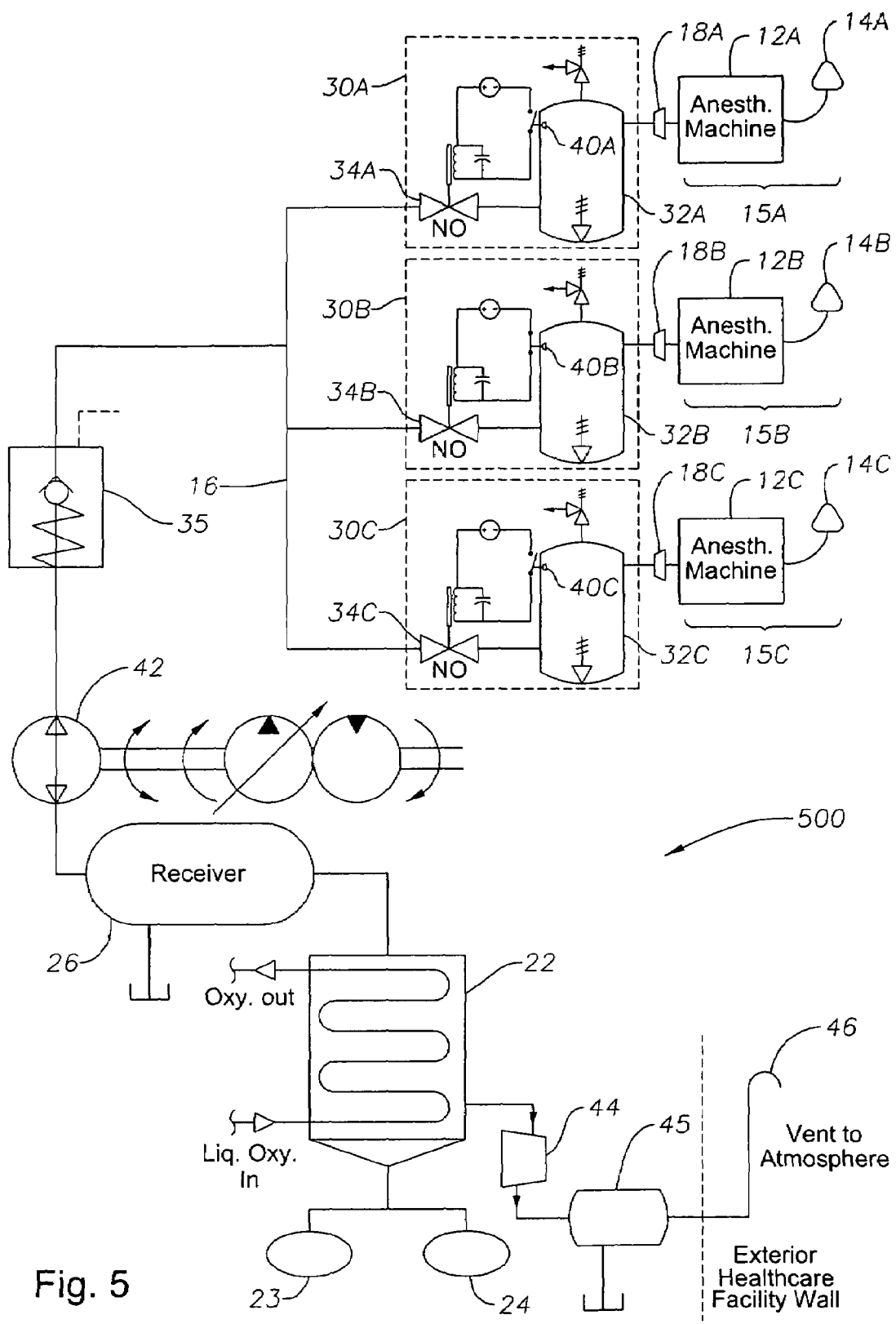
FIG. 5 illustrates in schematic form a preferred embodiment according to the invention of a low-flow waste anesthetic gas reclamation system which includes one or more low-flow waste anesthetic gas collection units, a compressor consisting of one or more compression stages, a single or multiple stage condenser/heat exchanger unit, and a small turbine to capture the potential energy of the compressed waste gas prior to atmospheric venting.

FIG. 5 illustrates a low-flow waste anesthetic gas collection and reclamation system 500 according to an alternative preferred embodiment of the invention for use in a hospital, surgical, dental, veterinary, or other healthcare facility. The reclamation system 500 is the same as the previously described reclamation system 200 of FIG. 2 except for the replacement of expansion valve 43 with turbine 44 and the inclusion of intelligent waste anesthetic gas collection units 30A, 30B, 30C located at or near each anesthetizing station 15A, 15B, 15C in the healthcare facility. As disclosed in co-pending application Ser. No. 11/266,966 by Berry, the intelligent waste anesthetic gas collection units 30A, 30B, 30C are preferably fluidly coupled within the individual legs of the collection manifold 16 near the standard waste anesthetic gas connectors 18A, 18B, 18C. Each intelligent gas collection unit 30A, 30B, 30C includes a collection chamber 32A, 32B, 32C, an exhaust valve 34A, 34B, 34C to selectively isolate the suction of the collection manifold 16 at the respective anesthetizing station when waste anesthetic gas is not being produced, and associated pressure sensors 40A, 40B, 40C, circuitry, controls, or mechanisms to operate the exhaust valve 34A, 34B, 34C. The collection chambers 32A, 32B, 32C may be rigid, flexible (such as an elastic bag), or a combination of both.

Referring to FIG. 5, waste anesthetic gas enters from the anesthetizing machine 12A, 12B, 12C exhaust into chamber 32A, 32B, 32C through a 19 mm, 30 mm, or similar standard anesthetic waste-gas connector 18A, 18B, 18C. Within the chamber 32A, 32B, 32C is a sensitive pressure sensor 40A, 40B, 40C electrically coupled to a solenoid-operated exhaust valve 34A, 34B, 34C located at the exhaust side of the chamber 32A, 32B, 32C. The pressure measured by pressure sensor 40A, 40B, 40C is the difference between the pressure of chamber 32A, 32B, 32C and the outside (ambient) air pressure. If the pressure within the chamber 32A, 32B, 32C rises to slightly above ambient, the increased pressure is detected by the pressure sensor 40A, 40B, 40C which by control circuitry causes the exhaust valve 34A, 34B, 34C to open. Opening valve 34A, 34B, 34C fluidly connects the chamber 32A, 32B, 32C to the vacuum source in collection manifold 16, resulting in a rapid decrease in pressure in chamber 32A, 32B, 32C. As the chamber pressure approaches ambient, the sensor 40A, 40B, 40C detects the pressure drop and causes the exhaust valve 34A, 34B, 34C to close.

The waste anesthetic gas collection manifold 16 operates at a slight vacuum pressure, e.g. 5 cm, which is generated by compressor 42. Therefore, isolating the collection manifold 16 from entraining room air when no waste anesthetic gas is being produced reduces the average anesthetic scavenging flow by approximately 90 percent and subsequently reduces the necessary capacity of the compressor 42, heat exchanger/condenser 22, piping, and associated other hardware. For a large hospital having between 20-30 operating rooms, it is estimated that waste anesthetic gas flow rate of 500-1000 l/min with the prior art reclamation system 10 of FIG. 1 is reduced to 50-100 l/min with the reclamation system 500 of FIG. 5. Furthermore, a low-flow scavenging system provides a more efficient means of waste anesthetic gas recovery through condensation, because a smaller volume of gas has to be cooled to the condensation temperatures of the individual anesthetic gases.

From vacuum manifold 16, the collected waste gas stream is passed through a check valve 35 to compressor 42. Compressor 42 has a single compression stage sized to elevate the pressure of the anesthetic waste gas from collection units 30A, 30B, 30C to a pressure above atmospheric pressure for subsequent treatment in a condensation unit 22. After compression, the waste anesthetic gas flows through a collection vessel or receiver 26 which allows any liquid condensed due to compression to be removed and separated from the compressed waste anesthetic gas stream. The compressed waste anesthetic gas stream is then cooled in a multi-stage condenser 22 such that the temperature of the nitrous oxide and other anesthetic halocarbons are lowered to a point where the vapors condense on the condenser coils 236B as a removal liquid (see disclosure with respect to FIG. 3). Alternatively, a single stage cold trap/fractionator 125 (FIG. 4) could be used to condense and collect the vapors as a frost on condenser coils 136 (FIG. 4) (see disclosure with respect to FIG. 4). The temperature and pressure at which the condensation process is conducted controls whether the anesthetic gas components are condensed as a removable liquid or deposited as a frost. The liquid anesthetic condensate is captured in a collection container 24A, 24B and the liquid water condensate is captured in a collection container 23.

As previously disclosed, the compressed waste gas is preferably first throttled through a small turbine 44 or similar device prior to atmospheric release 46 in order to capture the potential energy of the compressed waste gas. The captured energy may then be used to power the compressor 42 or supply other energy requirements of the method and system. Reducing the pressure of the compressed work anesthetic gas stream through turbine 44 may induce additional condensation of anesthetic components. Therefore, receiver 45 is provided to collect these anesthetic condensate prior to atmospheric discharge 46 of the remaining waste gas.

The Abstract of the disclosure is written solely for providing the United States Patent and Trademark Office and the public at large with a means by which to determine quickly from a cursory inspection the nature and gist of the technical disclosure, and it represents solely a preferred embodiment and is not indicative of the nature of the invention as a whole.

While some embodiments of the invention have been illustrated in detail, the invention is not limited to the embodiments shown; modifications and adaptations of the above embodiment may occur to those skilled in the art. Such modifications and adaptations are in the spirit and scope of the invention as set forth herein:

The invention claimed is:

1. A method of removing and separating gaseous anesthetics from a waste anesthetic gas stream to prevent atmospheric venting of gaseous anesthetics from a healthcare facility, said method comprising the steps of:

receiving said waste anesthetic gas stream from an anesthetizing machine (12A, 12B, 12C) into a chamber (32A, 32B, 32C), detecting a presence of said waste anesthetic gas stream received in said chamber,
periodically fluidly coupling said chamber to a collection manifold (16) via a selectively isolable flow path (34A, 34B, 34C) in response to said presence of said waste anesthetic gas stream received in said chamber when detected,
transferring said waste anesthetic gas stream received in said chamber to said collection manifold via said selectively isolable flow path, whereby said chamber and said selectively isolable flow path cooperate to minimize ingress of atmospheric gas into said collection manifold when no said waste anesthetic gas stream is exiting said anesthetizing machine,
compressing said waste anesthetic gas stream transferred to said collection manifold to a pressure above atmospheric pressure using a compressor (42) with at least one compression stage,
cooling said waste anesthetic gas stream by passing said waste anesthetic gas stream over a cooling surface (136, 236A, 236B) characterized by a surface temperature gradient such that said waste anesthetic gas stream passes thereover in a direction from a warmer to a colder temperature,
condensing said gaseous anesthetics from said waste anesthetic gas stream,
separating said condensed anesthetics from said waste anesthetic gas stream, and
venting to atmosphere said waste anesthetic gas stream absent said condensed anesthetics.

2. The method of claim 1 wherein said step of condensing said gaseous anesthetics from said waste anesthetic gas stream is conducted at a pressure and temperature to cause said gaseous anesthetics to be condensed as liquids.

3. The method of claim 1 wherein said step of condensing said gaseous anesthetics from said waste anesthetic gas stream is conducted at a pressure and temperature to cause said gaseous anesthetics to be condensed as solids.

4. The method of claim 3 wherein said condensing gaseous anesthetics undergo desublimation onto an outer surface of said cooling surface (136) such that said gaseous anesthetics with a higher desublimation point deposit on a warmer portion (160, 162) of said cooling surface (136) and said gaseous anesthetics with a lower desublimation point deposit on a colder portion (163, 164) of said cooling surface (136).

5. The method of claim 4 further comprising the step of:
heating said cooling surface (136) to selectively remove solid anesthetics thereon as liquid anesthetics such that said liquid anesthetics are sequentially separated and collected based upon melt point temperature.

6. The method of claim 1 further comprising the steps of:
expanding said waste anesthetic gas stream through an expansion valve (43) prior to atmospheric venting thereof, and
collecting in a receiver (45) liquefied anesthetic components condensed by expanding said waste anesthetic gas stream through said expansion valve.

7. The method of claim 1 further comprising the steps of:
expanding said waste anesthetic gas stream through a turbine (44) prior to atmospheric venting thereof, and
collecting in a receiver (45) liquefied anesthetic components condensed by expanding said waste anesthetic gas stream through said turbine.

8. A system for preventing atmospheric venting of anesthetic gas components of waste anesthetic gas from a healthcare facility, said system comprising:

a chamber (32A, 32B, 32C) for receiving said waste anesthetic gas from an anesthetizing machine (12A, 12B, 12C),
a detector (40A, 40B, 40C) coupled to said chamber for detecting a presence of said waste anesthetic gas received in said chamber,
a selectively isolable flow path (34A, 34B, 34C) arranged and designed to periodically fluidly couple said chamber to a collection manifold (16) in response to said presence of said waste anesthetic gas received in said chamber when detected by said detector, whereby said chamber and said selectively isolable flow path cooperate to minimize ingress of atmospheric gas into said collection manifold when no said waste anesthetic gas is exiting said anesthetizing machine,
said collection manifold (16) arranged and designed to draw said waste anesthetic gas from said chamber via said selectively isolable flow path into a compressor inlet,
a compressor (42) fluidly coupled to said compressor inlet and having at least one compression stage for elevating said waste anesthetic gas drawn into said compressor inlet to a pressure higher than atmospheric pressure,
a first heat exchanger/condenser (222A) having an inlet fluidly coupled to a flow line (239) from said compressor (42) and an outlet, said first heat exchanger/condenser also having a first cooling coil (236A) positioned therein with an outlet of said first cooling coil fluidly coupled to a refrigerant flow line (227) to a refrigerant sink, said first cooling coil having an inlet, and
a second heat exchanger/condenser (222B) having an inlet fluidly coupled to said outlet of said first heat exchanger/condenser (222A) and an outlet fluidly coupled to an atmospheric vent line (46), said second heat exchanger/condenser having a second cooling coil (236B) positioned therein with an outlet of said second cooling coil fluidly coupled to said inlet of said first cooling coil (236A) and an inlet of said second cooling coil fluidly coupled to another refrigerant flow line (221) from a refrigerant source (220), said first and second cooling coils providing a cooling surface characterized by a surface temperature gradient,
said first heat exchanger/condenser (222A) having a first vessel (23) in fluid communication therewith for collecting water liquefied from said waste anesthetic gas within said first heat exchanger/condenser, and
said second heat exchanger/condenser (222B) having a second vessel (24) in fluid communication therewith for collecting anesthetic components liquefied from said waste anesthetic gas within said second heat exchanger/condenser.

9. The system of claim 8 further comprising:
an expansion valve (43) fluidly coupled to said outlet of said second heat exchanger/condenser (222B), said expansion valve for reducing pressure of waste gas to be vented, and
a receiver (45) fluidly coupled between said expansion valve (43) and said atmospheric vent line (46), said receiver for collecting liquefied anesthetic components condensed by reducing said pressure of said waste gas.

10. A system for preventing atmospheric venting of anesthetic gas components of waste anesthetic gas from a healthcare facility comprising:
a chamber (32A, 32B, 32C) for receiving said waste anesthetic gas from an anesthetizing machine (12A, 12B, 12C), a detector (40A, 40B, 40C) coupled to said chamber for detecting a presence of said waste anesthetic gas received in said chamber, a selectively isolable flow path (34A, 34B, 34C) arranged and designed to periodically fluidly couple said chamber to a collection manifold (16) in response to said presence of said waste anesthetic gas received in said chamber when detected by said detector, whereby said chamber and said selectively isolable flow path cooperate to minimize ingress of atmospheric gas into said collection manifold when no said waste anesthetic gas is exiting said anesthetizing machine, said collection manifold (16) arranged and designed to draw said waste anesthetic gas from said chamber via said selectively isolable flow path into a compressor inlet, a compressor (42) fluidly coupled to said compressor inlet and having at least one compression stage for elevating said waste anesthetic gas drawn into said compressor inlet to a pressure higher than atmospheric pressure, and a heat exchanger/condenser (22) arranged and designed to remove said anesthetic gas components from said waste anesthetic gas, said heat exchanger/condenser having an inlet fluidly coupled to a flow line (139, 239) from said compressor (42) and an outlet fluidly coupled to an atmospheric vent line (46), said heat exchanger/condenser also having a cooling coil (136, 236A, 236B) positioned therein with an outlet of said cooling coil fluidly coupled to a refrigerant flow line (127, 227) to a refrigerant sink, said cooling coil having an inlet fluidly connected to another refrigerant flow line (121, 221) from a refrigerant source (120, 220), said cooling coil providing a cooling surface characterized by a surface temperature gradient, said heat exchanger/condenser (22) having at least one vessel (24A, 24B) in fluid communication therewith for collecting liquefied anesthetic components removed from said waste anesthetic gas within said heat exchanger/condenser (22).

11. The system of claim 10 further comprising:

an expansion valve (43) fluidly coupled to said outlet of said heat exchanger/condenser (22), said expansion valve for reducing pressure of waste gas to be vented, and a receiver (45) fluidly coupled between said expansion valve (43) and said atmospheric vent line (46), said receiver for collecting liquefied anesthetic components condensed by reducing said pressure of said waste gas.

12. The system of claim 10 further comprising:

a turbine (44) fluidly coupled to said outlet of said heat exchanger/condenser (22), said turbine for reducing pressure of waste gas to be vented, and a receiver (45) fluidly coupled between said turbine (44) and said atmospheric vent line (46), said receiver for collecting liquefied anesthetic components condensed by reducing said pressure of said waste gas.

13. The method of claim 1 wherein said step of condensing said gaseous anesthetics from said waste anesthetic gas stream is conducted at a pressure and temperature to cause at least one of said gaseous anesthetics to be condensed as a solid.

14. The system of claim 8 further comprising:

a turbine (44) fluidly coupled to said outlet of said second heat exchanger/condenser (222B), said turbine for reducing pressure of waste gas to be vented, and a receiver (45) fluidly coupled between said turbine (44) and said atmospheric vent line (46), said receiver for collecting liquefied anesthetic components condensed by reducing said pressure of said waste gas.

15. The system of claim 8 wherein, said selectively isolable flow path (34A, 34B, 34C) is a solenoid-operated exhaust valve.

16. The system of claim 10 wherein, said selectively isolable flow path (34A, 34B, 34C) is a solenoid-operated exhaust valve.

17. The system of claim 8 wherein, said detector (40A, 4GB, 40C) is a pressure sensor arranged and designed to measure a pressure increase in said chamber above ambient pressure.

18. The system of claim 10 wherein, said detector (40A, 40B, 40C) is a pressure sensor arranged and designed to measure a pressure increase in said chamber above ambient pressure.

19. The system of claim 10 wherein, said heat exchanger/condenser is arranged and designed to remove at least one of said anesthetic gas components from said waste anesthetic gas as a solid on said cooling coil.

20. The method of claim 1 wherein, said step of detecting a presence of said waste anesthetic gas stream received in said chamber is performed by a pressure sensor arranged and designed to measure a pressure increase in said chamber above ambient pressure, and said selectively isolable flow path (34A, 34B, 34C) is a solenoid-operated exhaust valve.

* * * * *